United States Patent [19]

Lang et al.

[11] Patent Number: 4,532,950
[45] Date of Patent: Aug. 6, 1985

[54] PROCESS FOR THE PERMANENT DEFORMATION OF HAIR

[75] Inventors: Günther Lang, Nieder-Beerbach; Theodor Wajaroff, Darmstadt, both of Fed. Rep. of Germany

[73] Assignee: Wella AG, Darmstadt, Fed. Rep. of Germany

[21] Appl. No.: 504,841

[22] PCT Filed: Jul. 11, 1980

[86] PCT No.: PCT/EP80/00049
§ 371 Date: Feb. 20, 1981
§ 102(e) Date: Feb. 20, 1981

[87] PCT Pub. No.: WO81/00203
PCT Pub. Date: Feb. 5, 1981

Related U.S. Application Data

[63] Continuation of Ser. No. 243,936, Feb. 20, 1981.

[30] Foreign Application Priority Data

Jul. 24, 1979 [DE] Fed. Rep. of Germany ....... 2929865

[51] Int. Cl.³ .............................................. A45D 7/00
[52] U.S. Cl. ........................................... 132/7; 424/72
[58] Field of Search .................... 132/7; 424/70–72

[56] References Cited

U.S. PATENT DOCUMENTS 3,142,623  7/1964  Zviak ....................................... 132/7
3,583,408  6/1971  Wall ......................................... 132/7
4,409,204 10/1983  Lang ................................... 132/7 X

OTHER PUBLICATIONS

*Cosmetics Science & Technology;* 1957; p. 620 (Excerpt from Chapt. 24 'Permnent Waving'.

*Primary Examiner*—A. J. Heinz
*Attorney, Agent, or Firm*—Michael J. Striker

[57] ABSTRACT

Process for the permanent deformation of hair, wherein the hair deforming agent as used, is prepared immediately before use, by commingling of two components. One component contains a hair keratin-reducing compound, while the other component consists of a minimum of one organic compound with activated multiple carbon-carbon bond or contains such compound. In given instances, inorganic redox catalysts are additionally contained. The ready-to-use deforming agent may, furthermore, contain redox indicators to allow determination of the usability of the hair keratin-reducing compound.

By commingling the two components to a ready-to-use hair deforming agent, the keratin-reducing compound is gradually bonded by adduction to the unsaturated aliphatic compound and thus being rendered unusable for hair deformation. The concentration of the keratin-reducing compound can thus be reduced in the course of the period of application and be adapted to the gradually softening hair.

3 Claims, No Drawings

PROCESS FOR THE PERMANENT DEFORMATION OF HAIR

This application is a continuation of application Ser. No. 243,936, filed Feb. 20, 1981.

The subject of the present invention is a process for the permanent deformation of hair, using therein a deforming agent containing a minimum of one organic compound with an activated aliphatic multiple carbon-carbon bond, said compound serving to gradually reduce the concentration of the keratin-reducing substance contained in said deforming agent.

In the processes customary at present, permanent deformation of hair ensues in two stages. Initially, the effect of a suitable reducing agent will cause splitting of the disulfide bridges of hair keratin. The hair is then brought into a new shape and subsequently fixed in the new shape by treatment with a suitable oxidant, with concomitant rebonding of the previously split disulfide bonds.

The agents used for the implementation of the first, reducing, process stage contain as the substance effective in deforming and reducing keratin, sulfite or certain mercapto compounds, particularly thioglycolic acid, thiolactic acid, also in the form of their salts with inorganic bases, as well as, respectively, thioglycerin or derivatives of said mercapto compounds. These agents are usually of alkaline nature in order to obtain softening of the hair and thus quick penetration of the keratin-reducing substance into the hair keratin.

The required alkalinity is obtained herein mainly by the addition of ammonia, organic amines, ammonium and alkaline carbonate, ammonium and alkaline hydrogen carbonate as well as alkaline hydroxides.

In order to obtain an adequate deformation of hair during the relatively short time in which these agents are effective upon the hair, the keratin-reducing substance effecting the deformation, as well as the aforenoted alkaline components of the preparations, must be used in large surplus quantities. The alkaline components remain fully active during the entire period of effectiveness. Their efficacy upon the gradually softening hair will, moreover, increase steadily in the course of the period of activity.

In the event that the aforedescribed reducing process stage is not interrupted in time and the reducing agent used therein is not thoroughly removed, the risk of damage to the hair will arise, for instance damage by excessive curling, breaking of hair or loss of hair. Hair that has been chemically damaged by previously effected permanent wave or dyeing treatment, and also thin hair, is particularly subject to such a risk. The different constitution of hair makes it therefore imperative to continually check the hair deformation obtained, this in order to determine the requisite period of activity.

Processes for the permanent deformation of hair are known, wherein the alkalinity is being continually increased during the reducing stage of the process, in order to avoid damage to the hair. A process is thus described in the German allowed application No. 1 089 124, wherein the alkalizing agent, ammonia, is being gradually rendered into an urea-containing deforming agent only by the addition of urease. The high concentration of the keratin-reducing component active in deforming, i.e. of the mercapto compound, will remain to a nearly unchanged extent herein.

The objective thus existed, of finding a process for the permanent deformation of hair which process, when compared to prior art, would allow a permanent, but hair-preserving, deformation.

This objective is attained to an outstanding degree by the process as per invention. The subject of the invention is thus a process for the permanent deformation of hair, wherein the hair is first being treated with a deforming agent, held in the desired shape, rinsed if needed, then being subjected to after-treatment with a fixing agent and rinsed, this process being characterized by using a deforming agent a mixture obtained from two components, with component 1 containing a substance reducing hair keratin whilst component 2 will employ a minimum of one organic compound containing an aliphatic multiple carbon-carbon bond and, furthermore, a carboxyl group bonded to said multiple bond either directly or by way of a methylene group and activated by a minimum of one multiple CO or CN bond conjugated to said multiple bond, with said organic compound being preferably selected from I. compounds with an activated double bond of the general formula

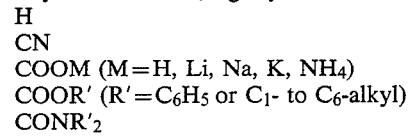

wherein the substituents $R^1$, $R^2$ and $R^3$ will, independently of each other, signify one of the rests H
CN
COOM (M=H, Li, Na, K, NH$_4$)
COOR' (R'=C$_6$H$_5$ or C$_1$- to C$_6$-alkyl)
CONR'$_2$

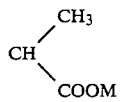

C$_6$H$_5$
C$_1$- to C$_6$-alkyl, with the substituent A constituting one of the rests COOM or CH$_2$COOM, wherein M is of the aforenoted significance, all this provided that A will signify CH$_2$COOM only when, at minimum, one of the constituents $R^1$, $R^2$ and $R^3$ will signify CN, COOM, COOR', CONR'$_2$, or selected from II. compounds with an activated triple bond of the general formula

wherein the substituent $R^4$ will signify one of the rests

H
CN
COOM
COOR'
CONR'$_2$.

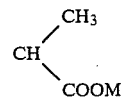

C₆H₅
C₁- to C₆-alkyl
and wherein the substituent A constitutes one of the rests COOM or CH₂COOM, with M being of the aforenoted significance, all this provided that A will signify CH₂COOM only then, when the substituent R⁴ is one of the rests CN, COOM, COOR' or CONR', or wherein use is being made of a preparation containing a minimum of one of the aforenoted organic compounds.

The component 1 of the aforenoted deforming agent, should contain as the hair keratin-reducing substance a sulfite, preferably an alkali or ammonia sulfite, or a mercapto compound, particularly thioglycolic acid or thiolactic acid, wherein such substance may also be in the form of salts with inorganic or organic bases.

The hair keratin-reducing substance in the deforming agent, should be contained therein in a proportion of approximately 1 to 15 percent by weight, preferably 5 to 12 percent per weight, all relative to the total quantity of said agent.

The following aliphatic carboxylic acids are examples for organic compounds with activated aliphatic carbon-carbon bond that may be contained in the deforming agent used in the process as per invention,
Aconitic acid,
acetylene dicarboxylic acid,
ethylene dicarboxylic acid
ethylmaleic acid
α-ethylcrotonic acid
i-amylmaleic acid
angelic acid
n-butylfumaric acid
n- and i-butylmaleic acid
citraconic acid
crotonic acid
fumaric acid
trans-glutaconic acid
isopropylmaleic acid
itaconic acid
maleic acid
mesaconic acid
α-methylitaconic acid
cis-β-methylglutaconic acid
trans-α-methylglutaconic acid
propiolic acid
cinnamic acid,
as are also the salts of these carboxylic acids with inorganic or organic bases, and furthermore their esters, partial esters, amides and nitriles.

The organic compounds with activated aliphatic multiple carbon-carbon bond should be contained therein in a quantity of approximately 1 to 20 percent by weight, preferably 1 to 10 percent by weight, relative to the total quantity of the deforming agent.

In order to accelerate the oxidizing effect of the atmospheric oxygen upon the keratin-reducing compound, component 2 of the deforming agent may contain redox catalysts such as transitional metal salts, particularly salts of manganese, iron and copper.

The deforming agent may, furthermore, contain organic redox indicators, such as, f.i., indigo, thionine, methylene blue and indigo carmine. The color of these indicators will allow recognizing such a state, if the reducing agent becomes unusable.

The redox catalysts may be contained in the deforming agent in a quantity of approximately 0.001 to 0.1 percent by weight, whilst the redox indicators may be present in a quantity of approximately 0.005 to 0.02 percent by weight.

The deforming agent may, furthermore, contain additives customary in hair deforming agents, such as alkalizing agents, particularly ammonia, organic amines, ammonium and alkali carbonates, ammonia and alkali hydrogen carbonates, as well as alkali hydroxides, wetting agents, soluents, emulgators, thickeners, swelling agents, fillers, colorants, perfume oils, and others.

Component 1 of this deforming agent may be prepared as a solution, a gel, a cream or an emulsion, whilst component 2 may, furthermore, also be present in solid state, for instance as powder, granulate or tablet.

Depending upon its composition, the deforming agent used in the process as per invention may be of a weakly acidic or also an alkaline reaction.

In the process as per invention for the permanent deformation of hair, the two components of the aforedescribed deforming agent are commingled immediately before use, the ready-to-use deforming agent thus obtained is then uniformly applied onto the hair, and the hair is then held in the desired shape (for instance by rolling the hair into curlers or by stretching it with a comb or brush). After an application period of approximately 10 to 50 minutes at a temperature of from 20° to 80° C., the remaining deforming agent is then, if necessary, rinsed off with water. The hair is subsequently fixed in its new shape with a customary fixing agent, such as, f.i. a 2% aqueous solution of hydrogen peroxide, and final thorough rinsing is then made with water.

The hair-preserving permanent deformation by using the process as per invention is made possible by the following sequence:

By commingling the two components of the deforming agent as used, immediately before application, the keratin-reducing compound x is gradually being bonded by adduction to the activated multiple bond of unsaturated aliphatic compound y, in accordance with the following examples of reactions, and thus rendered ineffective for hair deforming.

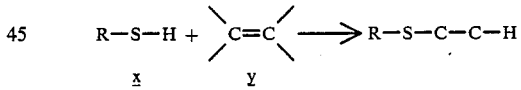

(R = molecular rest of mercapto-compound)

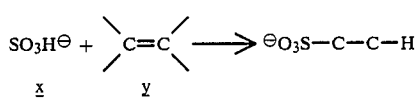

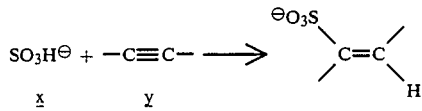

The above allows a timewise variation in the concentration of the keratin-reducing deformation-effecting compound, and selecting of the type and quantity of the two reactants will allow setting the concentration in such a manner that the high concentration of the keratin-reducing compound x required at the onset of the period in which the deforming agent is acting upon the hair, will be reduced at the desired rate during this period and thus adapt itself to the gradually softening hair.

The following embodiments will serve as closer explanation of the subject of the invention.

EMBODIMENTS

EMBODIMENT 1

A permanent-wave solution of the constitution

| Component 1 | |
|---|---|
| 10.0 g | thioglycolic acid |
| 8.0 g | ammonia, 25% |
| 6.1 g | ammonia hydrogencarbonate |
| 75.9 g | water |
| 100.0 g | | shows a pH value 8.2 and contains 10 percent by weight thioglycolic acid. If this permanent-wave preparation were to be used in a customary permanent-wave process, its efficacy would remain nearly unchanged. If, however, in the process as per invention, this solution (component 1) is provided immediately before use with an admixture of a powder (component 2) of the following constitution

| Component 2 | |
|---|---|
| 7.6865 g | Dilithiumfumarate |
| 0.0085 g | MnSO$_4$.H$_2$O |
| 0.0050 g | Indigo carmine |
| 7.7000 g | | whereby this admixture is dissolved in component 1 by shaking, the thioglycolic-acid content of the deforming agent thus obtained will be reduced at a temperature of 30° C. and within 20 minutes by 25% down to to 7.7 percent by weight, and within 40 minutes by 40% to 6 percent by weight, all relative to the respective initial content of thioglycolic acid in component 1.

The blue color of the deforming agent, caused by the indicator indigo carmine immediately after commingling the two components, will, after a short while, change to yellow and thus indicate the activity of the keratin-reducing constituent, i.e. the thioglycolic acid. Should component 1 not be able to function any more, for instance by its container having been left open or having suffered damage, this change in color would not occur.

In the process as per invention, the aforenoted deforming agent is uniformly applied unto the rolled hair immediately after having been obtained, and allowed to act for approximately 15 to 30 minutes. The hair is then rinsed with water and subjected to oxidative after treatment in the known manner. Finally, the curlers are being removed and the hair thoroughly rinsed with water.

A good waving effect will result, wherein the risk of damage to the hair and of skin irritations has been considerably reduced.

EMBODIMENT 2

For performing permanent waving of hair under preserving conditions, a preparation of the constitution

| Component 1 | |
|---|---|
| 15.40 g | monoethanolamine salt of thioglycolic acid, 50% aqueous solution, |
| 1.10 g | monoethanolamine |
| 1.00 g | octylphenol oxyethylated with 20 mol ethylene oxide, |
| 0.40 g | perfume oil |
| 0.01 g | 5,5' indigosulfonic acid, sodium salt, (indigo carmine) |
| 32.09 g | water |
| 50.00 g | | having a pH value 9.0 is optionally commingled with one of the two following preparations, each of which having a respective pH value 7.0,

| Component 2A | |
|---|---|
| 7.500 g | Itaconic acid |
| 0.003 g | FeSO$_4$.7H$_2$O |
| 7.800 g | ammonia, 25% |
| 34.697 g | water |
| 50.000 g | |
| Component 2B | |
| 3.800 g | itaconic acid |
| 0.003 g | FeSO$_4$.7H$_2$O |
| 4.000 g | ammonia, 25% |
| 42.197 g | water |
| 50.000 g | |

Commingling of component 1 with component 2A will result in a mild deforming agent for dyed hair.

Commingling of component 1 with component 2B will result in a deforming agent for normal hair.

Immediately after the deforming agent has thus been obtained, the hair is pre-moistened with it and then rolled onto curlers. Subsequently, heating clips heated to a temperature of 80° C. are attached to the curlers. After an application period of 10 minutes, the heating clips are removed. The hair is rinsed with water and oxidatively fixed in the known manner. The curlers are then removed and the hair thoroughly rinsed with water.

EMBODIMENT 3

A good permanent wave of hair is obtained under preserving conditions by commingling a solution constituted as

| Component 1 | |
|---|---|
| 10.90 g | Ammonium thioglycolate, 50% aqueous solution |
| 3.60 g | ammonia, 25% |
| 0.40 g | octylphenol, oxyethylated with 20 mol ethylene oxide |
| 0.01 g | 5,5' indigo-sulfonic acid, sodium salt, (indigo carmine) |
| 0.40 g | perfume oil |
| 34.69 g | water |
| 50.00 g | | having a pH value of 9.5, with a solution constituted as

| Component 2 | |
|---|---|
| 3.700 g | cinnamic acid |
| 0.008 g | MnSO$_4$.H$_2$O |
| 1.700 g | ammonia, 25% |
| 44.592 g | water |

| Component 2 | |
|---|---|
| 50.000 g | | and also of a pH value 9.5, then pre-moistening the hair with the ready-to-use deforming agent thus obtained, rolling the hair onto curlers and providing the curlers with heating clips preheated to 80° C. After an application period of 15 minutes, the heating clips are removed and the hair is then oxidatively fixed in the known manner. The hair is thoroughly rinsed with water after the curlers have been removed.

EMBODIMENT 4

Components 1 and 2 of a constitution as hereunder, are commingled immediately prior to commencing the permanent wave treatment.

| Component 1 | |
|---|---|
| 23.00 g | monoethanolamine salt of thioglycolic acid, 50% aqueous solution |
| 1.80 g | monoethanolamine |
| 0.80 g | octylphenol, oxyethylated with 20 mol ethylene oxide, |
| 0.01 g | 5,5' indigosulfonic acid, sodium salt, (indigo carmine) |
| 0.60 g | perfume oil |
| 23.79 g | water |
| 50.00 g | |

The pH value of this solution is 9.0.

| Component 2 | |
|---|---|
| 6.400 g | crotonic acid |
| 0.003 g | FeSO$_4$.7H$_2$O |
| 5.100 g | ammonia, 25% |
| 38.497 g | water |
| 50.000 g | |

The pH value of that solution is 7.0.

A ready-to-use deforming agent is obtained, having a pH value of 9.0. This deforming agent is applied onto the rolled-up hair and the hair covered with a hood made of synthetics. Heat is then applied onto the hair by means of a drying hood and the deforming agent allowed to act for approximately 15 minutes at a temperature of 45° C. Oxidative fixing in the usual manner is made thereupon. Thorough rinsing of the hair with water is made after removal of the curlers.

EMBODIMENT 5

For performing permanent wave treatment, a solution of the constitution

| Component 1 | |
|---|---|
| 22.8 g | ammonium sulfite, 35% |
| 19.6 g | sulfurous acid, 5% |
| 37.6 g | water |
| 80.0 g | | is commingled with a solution of the constitution

| Component 2 | |
|---|---|
| 8.000 g | citraconic acid |
| 0.006 g | FeSO$_4$.7H$_2$O |

| Component 2 | |
|---|---|
| 11.994 g | water |
| 20.000 g | | wherein component 2 was previously set with ammonia to a pH value of 6.7. A ready-to-use deforming agent is obtained. This deforming agent is uniformly applied onto hair that has been rolled onto curlers.

If the deforming agent is applied with atmospheric oxygen being excluded to a great extent (drying-hood wave), the sulfite content will be reduced to 88% of the initial value at a temperature of 45° C. and after 30 minutes of application, and to 78% of the initial value after 60 minutes of application.

If the deforming agent is applied under free access of atmospheric oxygen and at room temperature, (cold wave), the sulfite content will be reduced to 50% of the initial value already after an application of 20 minutes.

The period of application requisite for the respective treatment is determined herein with the use of a test curler.

The hair is finally rinsed with water, oxidatively fixed as usual and the curlers are removed. The hair is then thoroughly rinsed with water.

EMBODIMENT 6

De-curling of hair under preserving conditions is performed as follows:

Thorough commingling of a cream, constituted as

| Component 1 | |
|---|---|
| 14.24 g | Ammoniumthioglycolate, 50% aqueous solution, |
| 4.48 g | ammonia, 25% |
| 4.32 g | cetyl alcohol |
| 1.44 g | paraffin oil |
| 3.12 g | oleyl alcohol, oxyethylated with 20 mol ethylene oxide |
| 1.20 g | colloidal silica |
| 0.24 g | perfume oil |
| 50.96 g | water |
| 80.00 g | | with a pH value of 9.5, with a solution, constituted as

| Component 2 | |
|---|---|
| 3.714 g | maleic acid |
| 0.003 g | CuSO$_4$, anhydrous |
| 2.180 g | ammonia, 25% |
| 0.010 g | 3,9-bis-dimethylamino-phenazothionium chloride (methylene blue) |
| 14.093 g | water |
| 20.000 g | | the pH value of which has been set to 8, will produce a ready-to-use, creamy deforming agent of a thioglycolic acid content that is reduced within 5 minutes to 80% of the original value and within 10 minutes to 68% of same.

The creamy deforming agent thus obtained, is immediately and uniformly applied onto the hair to be de-curled. The hair will be combed until the desired de-curling has been obtained, thorough rinsing with water performed and oxidative fixing made in the usual manner. A final rinsing with water is then given.

This process offers good de-curling of hair, whilst avoiding, as far as possible, damage to skin and hair.

EMBODIMENT 7

For de-curling of hair under preservative conditions, a cream of the constitution

| Component 1 | |
|---|---|
| 12.40 g | ammonium thioglycolate, 50% aqueous solution, |
| 3.30 g | ammonium hydrogen carbonate |
| 3.90 g | oleylalcohol, ethoxylated with 20 mol ethylene oxide |
| 1.50 g | colloidal silica |
| 1.80 g | paraffin oil |
| 5.40 g | cetyl alcohol |
| 0.30 g | perfume oil |
| 61.40 g | water |
| 90.00 g | | of a pH value 8.2, is commingled with a solution, constituted as

| Component 2 | |
|---|---|
| 1.6 g | ammonium propriolate |
| 8.4 g | water |
| 10.0 g | | the pH value of which has been previously set with ammonia to 7, obtaining thereby a deforming agent in creamy form. In given instances, component 2 may merely consist of 1.6 g ammonium propiolate and thus be present in powdery form.

The deforming agent thus obtained is immediately applied onto the curled hair and the hair then combed smooth from time to time until the desired de-curling has been achieved. The hair is then rinsed with water and oxidatively fixed as usual. Subsequent rinsing with water is then performed.

All percentages cited in the present application represent percent by weight.

We claim:

1. Process for the permanent deformation of hair, comprising the steps of
   1. applying to the hair a freshly prepared aqueous composition obtained by mixture of two components
      (a) component 1 of which containing as a hair keratin reducing substance alkalisulfite, ammonium sulfite, thioglycolic acid, thiolactic acid or a water soluble salt of thioglycolic acid or thiolactic acid and
      (b) component 2 containing a compound selected from the group consisting of
         (i) carboxylic acids with activated double bonds of the formula

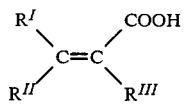

in which the substituents $R^I$ and $R^{II}$ represent H, COOH, $CH_2COOH$, $CH(CH_3)COOH$, $C_6H_5$ or $CH_3$, and $R^{III}$ represents H, $C_1$-$C_6$-alkyl or $CH_2COOH$, with the proviso that $R^I$ is different from $R^{II}$ and at least one of the substituents $R^I$ and $R^{II}$ represents COOH, or the salt thereof, and (ii) carboxylic acids with activated triple bonds of the formula $$HOOC-C\equiv C-R^{IV}$$

in which the substituent $R^{IV}$ has the meaning H or COOH, or the salt thereof;

2. holding the hair at a temperature of 20° to 80° C. for a time period of 10 to 50 minutes in the desired shape;
   3. fixing the hair in the desired shape by application of an aqueous hydrogen peroxide solution; and rinsing the hair.

2. Process according to claim 1, using as component 2 a preparation further comprising as redox catalyst a transition metal salt.

3. Process according to claim 1, using as one of said two components a preparation further comprising a redox indicator.

* * * * *